United States Patent
Shih

(10) Patent No.: US 7,857,620 B2
(45) Date of Patent: Dec. 28, 2010

(54) TOOTHBRUSH WITH AN ELECTRIC CIRCUIT

(75) Inventor: Shy-Ming Shih, No. 76-2, Sec. 2, Situn Rd., Taichung City (TW)

(73) Assignees: Shy-Ming Shih (TW); Kenneth Davidov; Yong Chen (CN)

( * ) Notice: Subject to any disclaimer, the term of this patent is extended or adjusted under 35 U.S.C. 154(b) by 189 days.

(21) Appl. No.: 11/797,097

(22) Filed: Apr. 30, 2007

(65) Prior Publication Data
US 2008/0120796 A1 May 29, 2008

(30) Foreign Application Priority Data
Nov. 28, 2006 (TW) ............... 95220902 U

(51) Int. Cl.
*A61C 1/00* (2006.01)
(52) U.S. Cl. ............... 433/29; 433/32; 15/167.1
(58) Field of Classification Search ........... 433/32, 433/80, 216, 29; 15/167.1
See application file for complete search history.

(56) References Cited

U.S. PATENT DOCUMENTS

| 534,528 | A |   | 2/1895  | Sonn |   |
|---|---|---|---|---|---|
| 2,834,344 | A |   | 7/1955  | Kanai |   |
| 3,478,741 | A |   | 11/1969 | Simor | 128/172.1 |
| 4,330,274 | A | * | 5/1982  | Friedman et al. | 433/29 |
| 4,526,570 | A |   | 7/1985  | Nakagawa et al. |   |
| 4,665,921 | A | * | 5/1987  | Teranishi et al. | 607/75 |
| 4,691,718 | A |   | 9/1987  | Sakuma | 132/84 |
| 4,726,806 | A |   | 2/1988  | Hukuba | 604/20 |
| 4,944,296 | A |   | 7/1990  | Suyama | 128/393 |
| 4,969,868 | A |   | 11/1990 | Wang | 604/20 |
| 5,133,102 | A | * | 7/1992  | Sakuma | 15/167.1 |
| 5,160,194 | A |   | 11/1992 | Feldman | 362/109 |
| 5,372,501 | A |   | 12/1994 | Shalvi | 433/32 |
| 6,106,294 | A |   | 8/2000  | Daniel | 433/216 |
| 6,341,400 | B1 | * | 1/2002  | Kobayashi et al. | 15/105 |
| 6,496,998 | B2 |   | 12/2002 | Moran | 15/105 |

(Continued)

FOREIGN PATENT DOCUMENTS

JP 402088002 A 3/1990

(Continued)

OTHER PUBLICATIONS

Image—Dr. Tung's "Ionic Toothbrush"; Distributed by Dr. Tung's Product, Inc., HI, USA; made in Japan; (1993) 2 pages.

(Continued)

*Primary Examiner*—Ralph A Lewis
*Assistant Examiner*—Eric Rosen
(74) *Attorney, Agent, or Firm*—St. Onge Steward Johnston & Reens LLC

(57) ABSTRACT

A toothbrush having a circuit for improving oral cavity health, displaying innovative light performance, allowing easy operation and reduced production cost. The toothbrush includes an electronic circuit disposed within a handle of the toothbrush, a power source, a light source, and a device to release ions. Ions are automatically generated within an oral cavity when a user holds the handle and wets the toothbrush with water, thus helping to maintain oral hygiene and providing a dazzling light performance emitted from the handle.

17 Claims, 2 Drawing Sheets

U.S. PATENT DOCUMENTS

| | | |
|---|---|---|
| 6,902,397 B2 | 6/2005 | Farrell .......................... 433/29 |
| 6,952,856 B2 | 10/2005 | Kaizuka ..................... 15/207.2 |
| 7,223,281 B2 | 5/2007 | Altshuler ..................... 607/90 |
| 7,354,448 B2 | 4/2008 | Altshuler ..................... 607/88 |
| 7,422,598 B2 | 9/2008 | Altshuler ..................... 607/93 |
| 2003/0054321 A1 | 3/2003 | Moran ........................ 433/215 |
| 2004/0172781 A1 | 9/2004 | Nakagawa ................... 15/105 |
| 2005/0183221 A1* | 8/2005 | Kemp et al. ................. 15/22.1 |
| 2006/0070195 A1 | 4/2006 | Morita ........................ 15/105 |
| 2006/0183071 A1 | 8/2006 | Hsuch ......................... 433/29 |
| 2006/0203486 A1* | 9/2006 | Lee et al. .................... 362/244 |
| 2007/0038272 A1 | 2/2007 | Liu .............................. 607/88 |
| 2007/0212665 A1 | 9/2007 | Jimenez ...................... 433/215 |
| 2007/0232983 A1 | 10/2007 | Smith ........................... 604/20 |
| 2008/0060154 A1 | 3/2008 | Jansheski ..................... 15/105 |
| 2008/0083074 A1 | 4/2008 | Taniguchi ................... 15/22.1 |
| 2008/0086189 A1 | 4/2008 | Taniguchi ................... 607/134 |
| 2008/0131834 A1 | 6/2008 | Shepherd ..................... 433/29 |
| 2009/0064429 A1* | 3/2009 | Hall et al. .................... 15/22.1 |

FOREIGN PATENT DOCUMENTS

| | | |
|---|---|---|
| JP | 4022414106 A | 9/1990 |
| JP | 402249505 A | 10/1990 |
| JP | 402277407 A | 11/1990 |
| JP | 402309908 A | 12/1990 |
| JP | 408080219 A | 3/1996 |
| JP | 409103326 A | 4/1997 |
| JP | 410080324 A | 3/1998 |
| JP | 02002325634 A | 11/2002 |
| JP | 02006180953 A | 7/2006 |

OTHER PUBLICATIONS

Image—Manufactured by: Hukuna Dental Corp. Japan; Distributed by: Dyna-Dental Systems, AZ; "Ionic hyG"; www.ionicbrush.com; (1993) 2 pages.

Image—Soladey-Eco "Light Activated Ionic Toothbrush"; Medium Bristle with replaceable head; www.soladey.com; Made in Japan; (1988) 2 pages.

Image—Family Tree Intl. Corp. Houston Texas;"The Ionizer—High Energy"; Made in China; (Jul. 2005) 2 pages.

* cited by examiner

TOOTHBRUSH WITH AN ELECTRIC CIRCUIT

BACKGROUND OF THE INVENTION (a) Field of the Invention

The present invention is relates to a toothbrush, and more particularly, one provided with a power source, a light source, and an electronic circuit to release electric ions to automatically generate ions into an oral cavity to help maintain oral hygiene.

(b) Description of the Prior Art

Conventional toothbrushes generally available in the market usually have multiple rows of bristles disposed on an end of a handle for removing residuals found in gaps between teeth to maintain oral health when used in conjunction with toothpaste. However, they fail to reach deeper to the skin in one's mouth to improve cellular activity. With rapid development of technology, toothbrushes having embedded electronic devices can be generally found in the market. The electronic devices, including circuits and associated electronic parts are essentially soldered together. Therefore, the electronic device is limited in function and deprived of becoming more practical in use by consumers.

The primary purpose of the present invention is to provide a toothbrush with a circuit that is capable of improving oral cavity health, displaying an innovative light performance, allowing easy operation and reducing production cost. To achieve these objectives, the toothbrush has an embedded power source connected to a circuit assembly provided with a light guide structure, and an ion generation device.

DETAILED DESCRIPTION OF THE PREFERRED EMBODIMENTS

Figure 1:
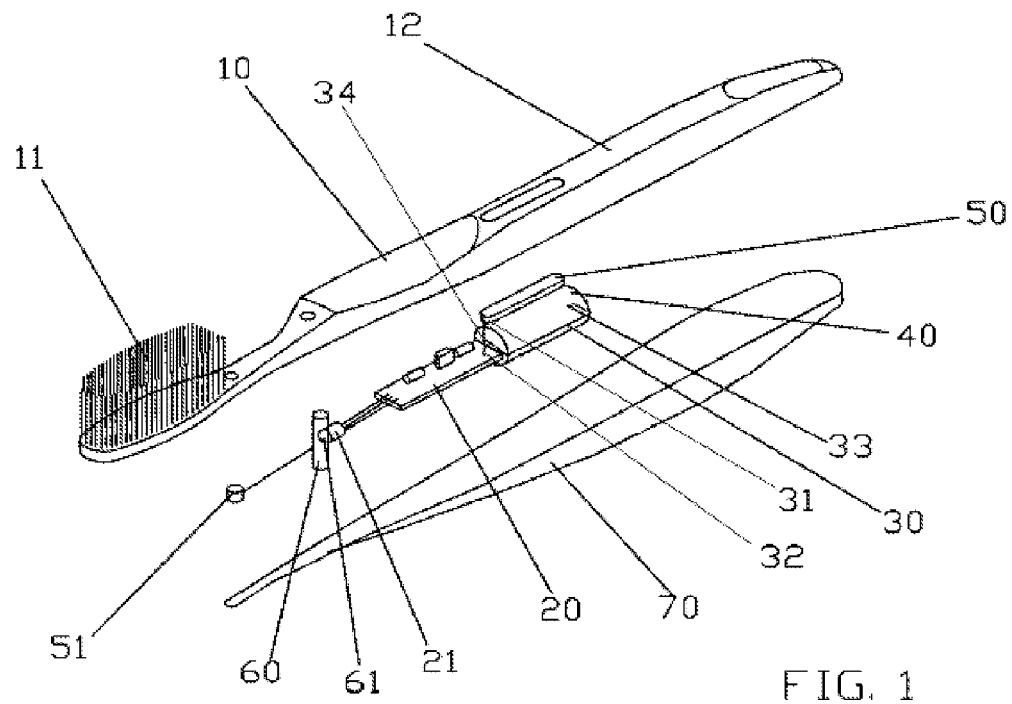
FIG. 1 is an exploded view of a first preferred embodiment of the present invention.

FIG. 1 shows an exploded view of a first preferred embodiment of the present invention, in which a control circuit 20 is disposed in a handle 12 of a toothbrush 10 having multiple rows of bristles 11. Conductive plates 30, 31 of different polarities are respectively connected to the control circuit. Contacts 32, 33 respectively protrude from conductive plates 30, 31 and contact positive and negative electrodes of cell 40. A signal electrode 34 extends from the conductive plate 31. A conductive plate 50 is disposed on and slightly protrudes from the handle 12 of the toothbrush 10. The signal electrode 34 is connected to the conductive plate 50.

A light-emitting device 21 is connected to the control circuit 20. A conductive block 51 is also connected to the control circuit 20 and is disposed near the end of the toothbrush 10 having the bristles 11. A light guide post 60 is located in the toothbrush 10 near to where the light-emitting device 21 is located. The light guide post 60 has a recessed light guide edge 61 disposed immediately next to a front end of the light-emitting device 21 such that light from light-emitting device 21 is visible through an exposed end of light guide post 60. The control circuit 20 of the toothbrush 10 is sealed in the handle 12 by a cover 70.

Figure 2:
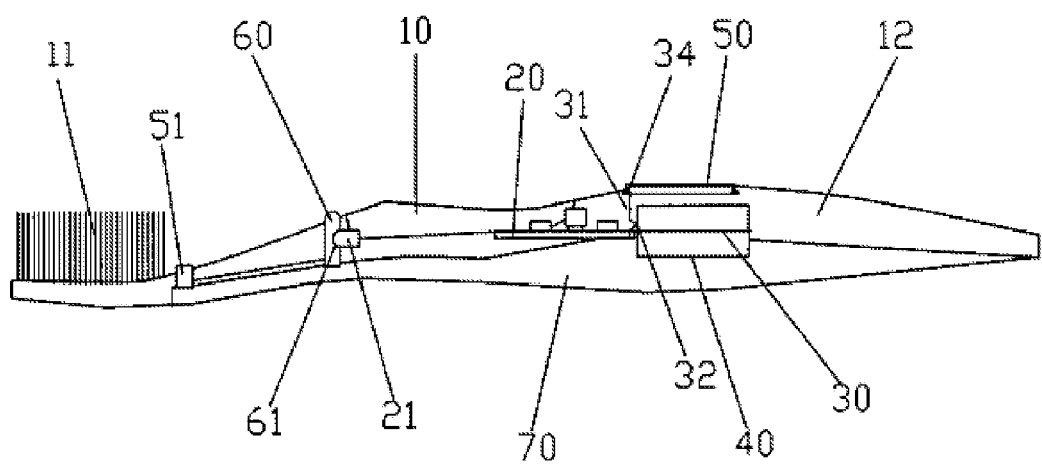
FIG. 2 is a perspective view of the first preferred embodiment of the present invention as assembled.

Now referring to FIG. 2, for a sectional view showing the preferred embodiment as assembled, wherein the conductive plate 31 on the control circuit 20 of the toothbrush 10 is provided with the contact 32 and the signal electrode 34 is in contact with the conductive plate 50. This structure saves soldering of multiple lines, a job otherwise required in the prior art, to reduce production cost. The conductive plate 50 and the conductive block 51 disposed in the handle of the toothbrush 10 enable, when the toothbrush is held and dipped in water by a user, the control circuit 20 to be automatically operated to generate ions near the bristles 11 for cleaning the oral cavity of the user and, at the same time, to automatically cause the light-emitting device 21 to illuminate. The light-emitting device 21 may be a monochromatic or a multi-color light source adjacent to the light guide edge 61 of the light guide post 60. One end or both ends of the light guide post 60 are slightly exposed out of the toothbrush handler to enable light from the light-emitting device 21 to be visible externally of the toothbrush 10 to prompt the user that the toothbrush 10 is in use. If the toothbrush 10 and/or the cover 70 is made of a material that is capable of refracting or guiding light, the toothbrush may provide unique light and shade performance effects when the light-emitting device 21 is activated to emit light.

Figure 3:
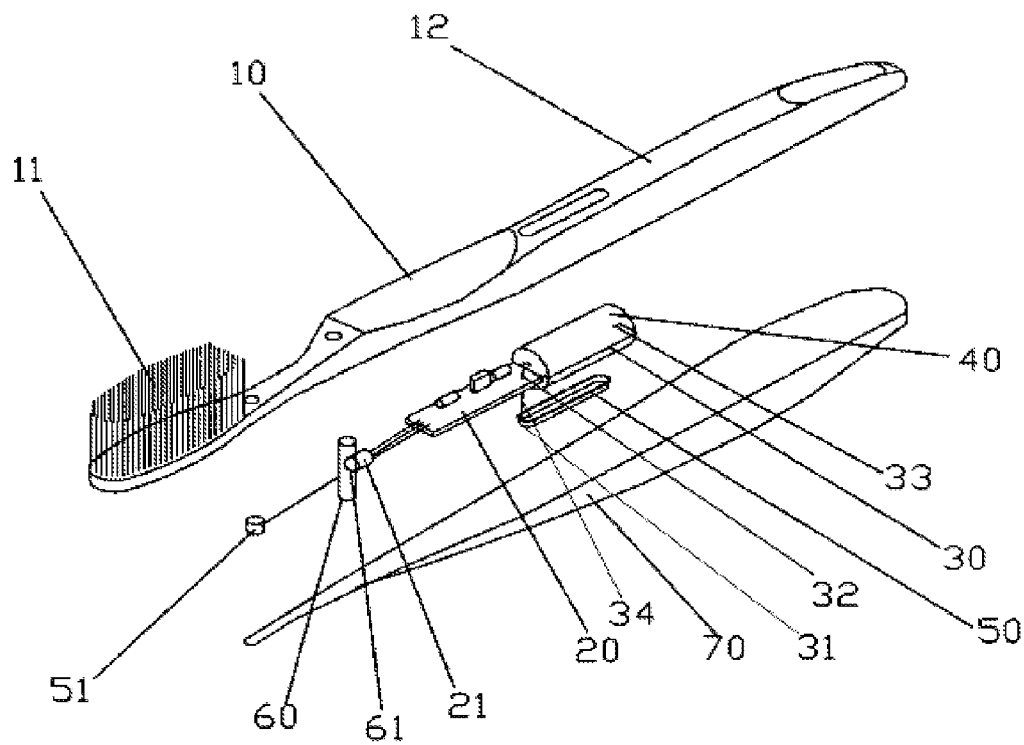
FIG. 3 is an exploded view of a second preferred embodiment of the present invention.
Figure 4:
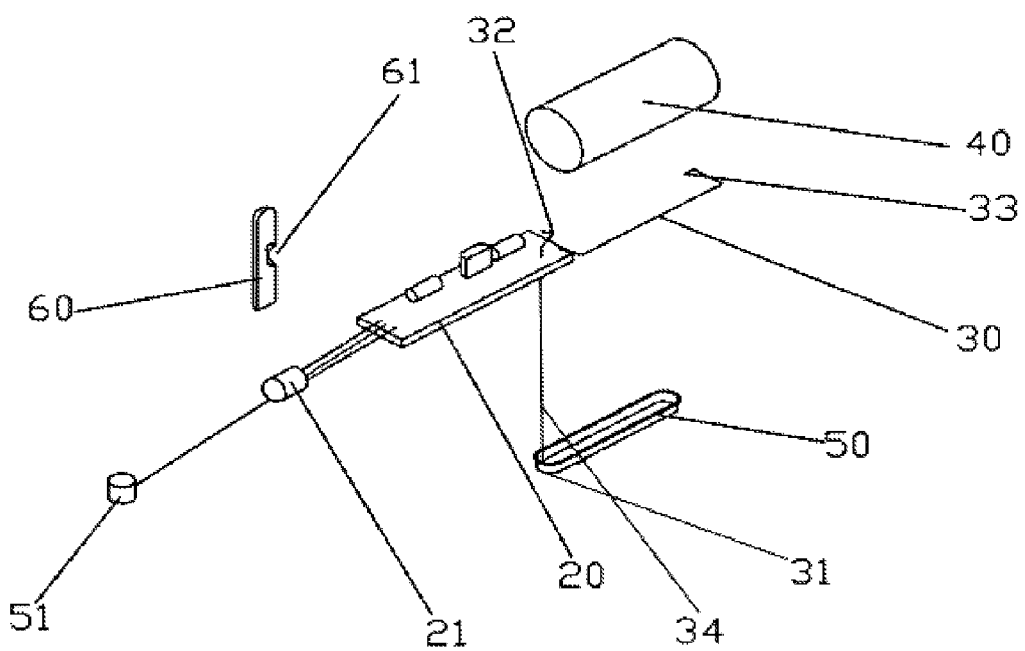
FIG. 4 is an exploded view showing an electronic device of the second preferred embodiment of the present invention.

FIGS. 3 and 4 show a second preferred embodiment of the present invention, in which the same results can be achieved by having the conductive plate 50 disposed on the cover 70 beneath the control circuit 20 and having the conductive plates 31, 50 in conductive contact with each other.

The present invention discloses a toothbrush including an electronic circuit disposed within a handle of the toothbrush and includes a combination of a power source connected to the circuit, a light guide structure and an ion generation device. The toothbrush achieves its purposes of maintaining oral hygiene, displaying innovative color performance effects, allowing easy operation, and reducing production cost to add more practical and economic values to the toothbrush.

I claim:

1. A toothbrush comprising:
   a handle;
   said handle comprising a continuous portion of at least 50% comprising a continuous portion of a light guiding and light refracting material, and having a first side and a second side opposite said first side; wherein said continuous portion comprises at least 50% of said handle;
   a plurality of bristles extending from said first side and adjacent to a first end;
   a single electronic circuit consisting essentially of:
      a first conductive member mounted in said handle adjacent to said plurality of bristles having a portion extending outward from said handle;
      an electronic control circuit embedded in said handle electrically connected to said first conductive member;
      a second conductive member mounted in said handle;
      a source of electrical power mounted within said handle electrically connected to said electronic control circuit and said second conductive member; and
      a single light source visible through all of said light guiding and light refracting material;
   wherein said single electronic circuit activates said source of electrical power and said light source when said second conductive member is gripped by a user and said first conductive member is moistened.

2. The toothbrush of claim 1 wherein said light source is a monochromatic light source.

3. The toothbrush of claim 1 wherein said light source is a multi-color light source.

4. The toothbrush of claim 1 wherein the light source emits unique light and shade performance effects when the light source is activated.

5. The toothbrush of claim 1 wherein said light source comprises a light emitting device electrically connected to said electronic control circuit, and a light guide post mounted to said handle located adjacent to said light emitting device, said light guide post having a portion extending exteriorly of said handle so as to transmit light from said light emitting device, wherein said light source is visible through said light guide post and said light guiding and refracting material.

6. The toothbrush of claim 5 wherein said light guide post comprises a recessed light guide edge located adjacent to said light emitting device.

7. The toothbrush of claim 1 wherein said toothbrush is an ionic toothbrush.

8. The toothbrush if claim 1 wherein ions are emitted from said first conductive member.

9. The toothbrush of claim 1 wherein said second conductive member is located on said first side.

10. The toothbrush of claim 1 wherein said second conductive member is located on said second side.

11. The toothbrush of claim 1 wherein said second conductive member protrudes from said handle.

12. An Ionic toothbrush comprising:
a handle;
said handle comprising a continuous portion of at least 50% handle comprising a continuous portion of a light guiding and light refracting material, and having a first side and a second side opposite said first side; wherein said continuous portion comprises at least 50% of said handle;
a plurality of bristles extending from said first side and adjacent to a first end;
a single electronic circuit consisting essentially of:
a first conductive member mounted in said handle adjacent to said plurality of bristles having a portion extending outward from said handle;
an electronic control circuit embedded in said handle electrically connected to said first conductive member;
a second conductive member mounted in said handle;
a source of electrical power mounted within said handle electrically connected to said electronic control circuit and said second conductive member;
a single light source visible through said light guiding and light refracting material; all of said light guiding and light refracting material;
wherein said single electronic circuit activates said source of electrical power and said light source, and ions are emitted from said first conductive member, when said second conductive member is gripped by a user and said first conductive member is moistened.

13. The toothbrush of claim 12 wherein said light source is a monochromatic light source.

14. The toothbrush of claim 12 wherein said light source is a multi-color light source.

15. The toothbrush of claim 12 wherein the light source emits unique light and shade performance effects when the light source is activated.

16. The toothbrush of claim 12 wherein said light source comprises a light emitting device electrically connected to said electronic control circuit, and a light guide post mounted to said handle located adjacent to said light emitting device, said light guide post having a portion extending exteriorly of said handle so as to transmit light from said light emitting device, wherein said light source is visible through said light guide post and said light guiding and light refracting material.

17. The toothbrush of claim 16 wherein said light guide post comprises a recessed light guide edge located adjacent to said light emitting device.

* * * * *

UNITED STATES PATENT AND TRADEMARK OFFICE
CERTIFICATE OF CORRECTION

PATENT NO. : 7,857,620 B2
APPLICATION NO. : 11/797097
DATED : December 28, 2010
INVENTOR(S) : Shy-Ming Shih Page 1 of 1

It is certified that error appears in the above-identified patent and that said Letters Patent is hereby corrected as shown below:

Column 2, Claim 1:
In line 45, "said handle comprising a continuous portion of at least 50% comprising a continuous portion of a light guiding and light refracting material" should be changed to --said handle comprising a continuous portion of a light guiding and light refracting material--.

Column 3, Claim 12:
In line 33, "said handle comprising a continuous portion of at least 50% handle comprising a continuous portion of a light guiding and light refracting material" should be changed to --said handle comprising a continuous portion of a light guiding and light refracting material--.

Column 4, Claim 12:
In line 12, "a single light source visible through said light guiding and light refracting material all of said light guiding and light refracting material" should be changed to --a single light source visible through all of said light guiding and light refracting material--.

Signed and Sealed this
Twenty-first Day of February, 2012

David J. Kappos
*Director of the United States Patent and Trademark Office*